United States Patent

Meguro et al.

[11] Patent Number: 4,771,050
[45] Date of Patent: Sep. 13, 1988

[54] THIOLACTAM-N-ACETIC ACID DERIVATIVES

[75] Inventors: Kanji Meguro, Nishinomiya; Hitoshi Ikeda, Higashiosaka; Yujiro Yamamoto, Suita, all of Japan

[73] Assignees: Takeda Chemical Industries, Ltd.; Senju Pharmaceutical Co., Ltd., both of Osaka, Japan

[21] Appl. No.: 37,785

[22] Filed: Apr. 13, 1987

[30] Foreign Application Priority Data

Apr. 17, 1986 [JP] Japan ............................ 61-89295
Jun. 20, 1986 [JP] Japan ............................ 61-145941

[51] Int. Cl.$^4$ .................. A61K 31/535; A61K 31/54; C07D 265/36; C07D 279/16
[52] U.S. Cl. ........................ 514/224.2; 514/230.5; 544/52; 544/105
[58] Field of Search ............. 514/225, 228; 544/52, 544/105

[56] References Cited

FOREIGN PATENT DOCUMENTS 162776 11/1985 European Pat. Off. .
1173942 12/1969 United Kingdom .

Primary Examiner—Richard L. Raymond
Attorney, Agent, or Firm—Wenderoth, Lind & Ponack

[57] ABSTRACT

Compounds of the general formula:

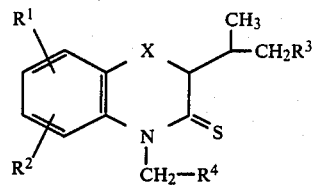

wherein, $R^1$ and $R^2$ are, the same or different, hydrogen, a halogen, a lower alkyl, a cycloalkyl, a lower alkoxy, trifluoromethyl or a phenylalkyloxy whose phenyl ring may be substituted by one to three substituents selected from the group consisting of a halogen, a lower alkyl, a lower alkoxy, methylenedioxy and trifluoromethyl; $R^3$ is hydrogen or methyl; $R^4$ is carboxyl or an esterified carboxyl; and X is oxygen or sulfur, or a salt thereof. These compounds possess aldose reductase inhibitory and platelet aggregation inhibitory activities, and are of use as drugs for prevention and treatment of diabetic complications such as diabetic cataract, retinophathy, nephropathy, and neuropathy.

8 Claims, No Drawings

THIOLACTAM-N-ACETIC ACID DERIVATIVES

This invention relates to a novel condensed thiolactam-N-acetic acid derivative having excellent aldose reductase inhibitory and platelet aggregation inhibitory activities. The compound of this invention is useful for prevention and treatment of diabetic complications such as diabetic cataract, retinopathy, nephropathy, and neuropathy.

Japanese patent application Laid-Open No. 40264/86 describes that various 3-thioxo-1,4-benzoxazine-4-acetic acid derivatives and 3-thioxo-1,4-benzothiazine-4-acetic acid derivatives exert aldose reductase inhibition and are useful for treatment of peripheral disturbance due to diabetes (cataract, diabetic neuropathy). However all of the compounds concretely described in this publication are only weakly inhibitory to sorbitol accumulation when administered orally to diabetic animals, and therefore are not satisfactory for practical application as medicines.

The inventors found, as a result of their research on the compounds described above and related compounds that special compounds which are not described in Japanese patent application Laid-Open No. 40264/86 are strongly inhibitory in vivo to sorbitol accumulation and also have platelet aggregation inhibitory property.

This invention relates to

1. A compound having the general formula

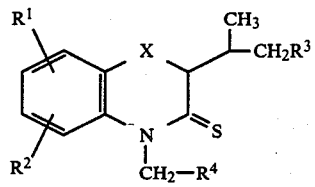

wherein, $R^1$ and $R^2$ are, the same or different, hydrogen, a halogen, a lower alkyl, a cycloalkyl, a lower alkoxy, trifluoromethyl or a phenylalkyloxy whose phenyl ring may be substituted by one to three substituents selected from the group consisting of a halogen, a lower alkyl, a lower alkoxy, methylenedioxy and trifluoromethyl; $R^3$ is a hydrogen or methyl; $R^4$ is carboxyl or an esterified carboxyl; and X is oxygen or sulfur, or a salt thereof, 2. A therapeutic agent for diabetic complications, containing a compound having the general formula (I), or a pharmaceutically acceptable salt thereof, 3. A method for producing a compound having the general formula:

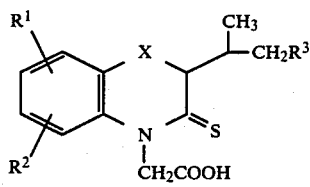

wherein each symbol has the meaning given above, or a salt thereof, which comprises hydrolyzing a compound having the general formula:

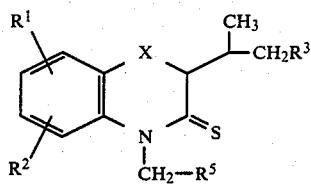

wherein, $R^1$, $R^2$, $R^3$ and X are the same as described above, and $R^5$ is an esterified carboxyl, and 4. A method for producing a compound having the general formula (Ib), which comprises reacting a compound having the general formula:

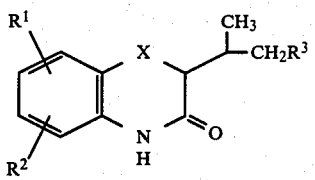

wherein each symbol has the meaning given above, with a compound having the general formula:

$$Y^1CH_2R^5 \quad (III)$$

wherein $Y^1$ is a halogen and $R^5$ has the meaning given above, to give a compound having the general formula:

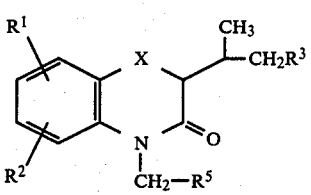

wherein each symbol has the meaning given above, and then reacting the resulting compound with a thionating agent.

In the above general formulas the lower alkyl represented by $R^1$ and $R^2$ is favorably a straight chain or branched one having 1 to 6 carbon atoms, such as methyl, ethyl, propyl, isopropyl, butyl, isobutyl, sec-butyl, tert-butyl, pentyl, isopentyl, neopentyl, tert-pentyl, hexyl, and isohexyl; the lower alkoxy group is one having 1 to 6 carbon atoms and includes those formed by binding an oxygen atom to the alkyl group described above. The cycloalkyl represented by $R^1$ and $R^2$ is favorably the one having 3-7 carbon atoms, such as cyclopropyl, cyclobutyl, cyclopentyl, cyclohexyl, and cycloheptyl. The halogen represented by $R^1$ and $R^2$ includes fluorine, chlorine, bromine and iodine, among which fluorine and chlorine are preferable. The phenylalkyloxy represented by $R^1$ and $R^2$ is favorably one having 7-9 carbon atoms, such as benzyloxy, 1-phenylethoxy, 2-phenylethoxy, 1-phenylpropyloxy, 2-phenylpropyloxy, and 3-phenylpropyloxy. These groups may have a substituent or substituents on their benzene ring, and such substituent includes a halogen (e.g. fluorine, chlorine, bromine, iodine), a lower alkyl (e.g. methyl, ethyl, propyl, isopropyl), a lower alkoxy (e.g. methoxy, ethoxy, propoxy, isopropoxy), methylenedioxy, and trifluoromethyl. One to three of these substituents may be present on the benzene ring, and two or more substituents on the ring may be the same or different. $R^1$ and $R^2$ may be present at any position in the benzene ring, but favorably at 6-, 7- or 8-position. In particular, when either $R^1$ or $R^2$ is alkyl or cycloalkyl, the 8-position is the most favorable position for alkyl or cycloalkyl. Among compounds (I), 1,4-benzoxazine where X is oxygen is preferable to 1,4-benzothiazine where X is sulfur.

The esterified carboxyl represented by $R^4$ and $R^5$ includes an alkoxycarbonyl having 2 to 6 carbon atoms (e.g. methoxycarbonyl, ethoxycarbonyl, propoxycarbonyl, isopropoxycarbonyl, butoxycarbonyl, isobutoxycarbonyl), an aryloxycarbonyl having 7 to 9 carbon atoms (e.g. phenoxycarbonyl, p-methylphenyloxy carbonyl) and aralkyloxycarbonyl having 8 to 10 carbon atoms (e.g. benzyloxycaronyl).

As the halogen represented by $Y^1$ in the formula (III), chlorine, bromine and iodine are mentioned.

The salt of the compound having the general formula (Ia), particularly a pharmaceutically acceptable salt, includes an alkali metal salt (e.g. sodium salt, potassium salt), an alkaline earth metal salt (e.g. calcium salt), and aluminum salt.

The compound having the general formula (I) or the salt thereof has an asymmetric carbon atom, and hence forms optical isomers or diastereomers. The isomers may be obtained in their pure form if necessary. Resolution of a pair of diastereomers may be accomplished by a usual method such as fractional crystallization and chromatography on, for example, silica gel. Optical resolution of a racemate into its mirror image components may also be accomplished by a usual method such as salt formation of (Ia) with an optically active base (e.g. quinine, quinidine, cinchonine, cinchonidine, 1-phenylethylamine) followed by selective crystallization or fractional crystallization and then neutralization with an appropriate acid (e.g. hydrochloric acid, hydrobromic acid, sulfuric acid) to give a free acid. Optical resolution of (Ia) may also be carried out by (1) converting (Ia) to its ester with an optically active alcohol (e.g. methyl lactate, ethyl lactate, 1-phenylethyl alcohol, menthol), (2) separating the diastereo esters by recrystallization or by chromatography, and then (3) hydrolyzing each diastereo ester to give each mirror image isomer of (Ia). Condensation of (Ia) with an optically active alcohol is, for example, carried out in a solvent (e.g. dichloromethane, chloroform, ethyl acetate, dimethylformamide), using a condensing agent (e.g. dicyclohexylcarbodiimide) in the presence of 4-dimethylaminopyridine at about 0°–60° C. Hydrolysis of the diastereo ester of (Ia) to the optically active (Ia) is conducted in the same manner as the hydrolysis of (Ib) which will be mentioned later. The (S)-isomer is more preferable to (R)-isomer in inhibiting aldose reductase.

The compound having the general formula (I) and the salt thereof are novel compounds which are not found in the literature, and are strongly inhibitory to aldose reductase of mammals (e.g. mouse, rat, rabbit, dog, cat, bovine, human). Aldose reductase is known to reduce, for example, glucose into sorbitol and therefore to accelerate accumulation of sorbitol in the tissues such as blood vessels, nerve and lens, causing various complications in diabetic patients. The compound (I) of this invention and the salt thereof have been proved not only to inhibit strongly the said enzyme in vitro, but also to be chemically stable, be absorbed well through the digestive tract, and be well distributed into the tissues. Therefore the compound (I) and salt thereof are very effective in inhibiting sorbitol accumulation in the tissues of streptozocininduced diabetic rat when given orally. The compound (I) and salt thereof also have platelet aggregation inhibitory activity. It is assumed that increased platelet aggregation often seen in diabetic patients may be one of the causes of diabetic microangiopathy such as retinopathy and nephropathy. Therefore compound (I) and salt thereof are expected to be useful in treating the increased platelet aggregation to prevent such complications.

The compound having the general formula (I) and the pharmaceutically acceptable salt thereof are only slightly toxic whether given acutely or chronically, and therefore very useful as medicines for prevention and treatment of diabetic complications in man (cataract, retinopathy, nephropathy, neuropathy, etc.).

The compound having the general formula (I) and the pharmaceutically acceptable salt thereof may, when used as the medicines described above, be orally or parenterally given in the form of powder, granule, tablet, capsule or injection, prepared by mixing with pharmaceutically acceptable carriers, excipients (e.g. lactose, starch, sugar, magnesium stearate), or diluents (e.g. water), and also in the form of eye drop or eye ointment when used as therapeutic agents for cataract. The dose varies according to the nature of the compound, route of administration, symptoms, age and body weight of the patient, etc.; for example, for oral administration to an adult diabetic patient, the daily dose is about 50 to about 1500 mg, preferably about, 100 mg to about 1000 mg, which is favorably divided into 1 to 3 doses. In the case of an eye drop composition, it is desirable that a formulation or a suspension containing about 0.001–1% of the active component is given 3–5 times a day at the dose of one to several drops at a time. In the case of eye ointment, a formulation prepared by mixing about 0.001–1% of the active component in a usual eye ointment base is given about 1–4 times a day according to the symptoms.

The compound having the general formula (Ia) and the salt thereof can be produced by hydrolysis of the compound having the general formula (Ib). The said hydrolysis is conducted favorably in a solvent in the presence of an alkali such as sodium hydroxide and potassium hydroxide. Such solvents include alcohols such as methanol, ethanol, propanol, 2-propanol, and methoxyethanol, ethers such as dioxane, tetrahydrofuran, and dimethoxyethane, and mixtures of these solvents with water. The hydrolysis can be conducted usually at about 0°–100° C., preferably about 10°–60° C., and the amount of the alkali used is about 1–5 moles, preferably about 1.1–3 moles, per 1 mole of the compound (Ib) used. In the case of 3,4-dihydro-3-thioxo-2H-1,4-benzoxazine-4-acetic acid esters having no substituent or a straight chain alkyl group at the 2-position, the 2-oxo derivative is also produced abundantly as by-product owing to simultaneous hydrolysis of the 2-thioxo group while the esters are hydrolyzed. Therefore the yield is low and purification is difficult with such compounds. On the other hand, the compound (Ib) having an oxygen atom as X is resistant to such side reaction because of the α-branched structure of the substituent at the 2-position, and therefore has an advantage in production that not only the desired product (Ia) is obtained in good yield but also purification of (Ia) is easy. For example, crystalline product is obtained either by concentration of the reaction mixture followed by dilution with water and then acidification with hydrochloric acid, or by extraction with an appropriate solvent (e.g. ethyl acetate) after acidification, followed by concentration. The crystalline product can be purified further by recrystallization or by chromatography if necessary. The compound (Ia) having a sulfur atom as X is also chemically stable, and can be isolated and purified in a similar manner. The compound (Ia) can be converted into a salt because it has a carboxylic acid residue. When an optically active starting compound (Ib) is used, an optically active product (Ia) or a salt thereof can be obtained.

The compound having the general formula (Ib) can be produced by the following procedure. (Process 1)

The compound (IV) can be produced by the reaction of the compound (II) with a halogenoacetic acid ester (III). This reaction is conducted in an appropriate solvent in the presence of a base. Such solvents include tetrahydrofuran, dimethoxyethane, dioxane, N,N-dimethylformamide, and dimethylsulfoxide, and such bases include sodium methoxide, sodium ethoxide, potassium t-butoxide, sodium hydride, potassium hydride, sodium amide, etc. It is desirable that in this reaction the compound (II) is allowed to react with a base to form an anion of compound (II) which is then allowed to react with the compound (III). The reaction temperature is about $-10°–100°$ C., preferably about $0°–60°$ C. The amounts of the base and the compound (III) used are about 1–1.5 moles per 1 mole of the compound (II).

(Process 2)

The compound (IV) obtained in the (Process 1) is allowed to react with a thionating agent to give the compound (Ib). This reaction can be conducted in a solvent in the presence of a thionating agent. As the solvent, aromatic hydrocarbons such as benzene, toluene, xylene, and chlorobenzene, ethers such as tetrahydrofuran and methoxyethane, halogenated hydrocarbons such as chloroform, dichloromethane, and dichloroethane, and pyridine are mentioned. Thionating agent used includes phosphorus pentasulfide, Lawesson reagent, and Davy reagent. The reaction is conducted usually at about $10°–150°$ C., preferably at about $20°–130°$ C. The amount of the thionating agent used is about 0.5–3 moles, preferably about 1–2 moles, per 1 mole of the compound (IV).

The compound (II) in which X is an oxygen atom can be produced, for example, by the method described in Journal of Medicinal and Pharmaceutical Chemistry, 5, 1378 (1962) or by a method in accordance with said method, via the route (Procedure A) described in the following.

Procedure A

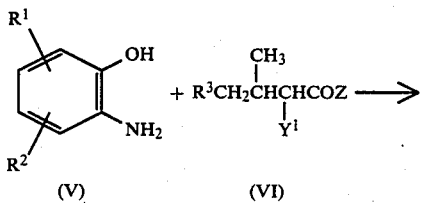

(V)        (VI)

-continued
Procedure A

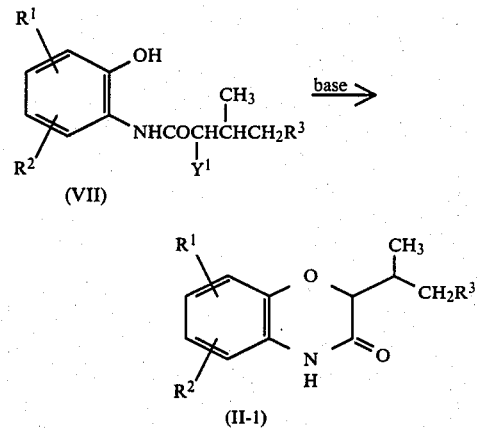

(VII)

(II-1)

wherein Z is a chlorine or a bromine atom and the other symbols are the same as described above.

The compound (II) in which X is a sulfur atom can be produced, for example, by the following methods (Procedure B or Procedure C).

Procedure B

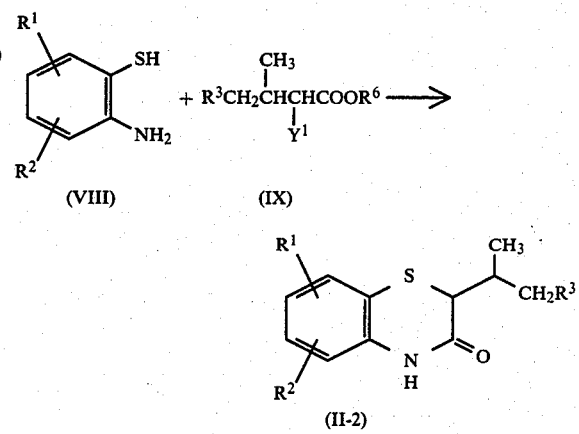

(VIII)        (IX)

(II-2)

wherein $R^6$ is a hydrogen or a lower alkyl having 1 to 4 carbon atoms and the other symbols are the same as described above.

Procedure C

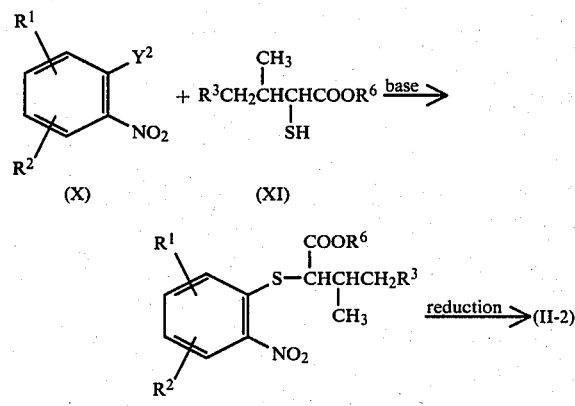

(X)        (XI)

(XII)

wherein $Y^2$ is a halogen atom and the other symbols are the same as described above.

In the reaction formulas described above, the lower alkyl group represented by $R^6$ includes methyl, ethyl, propyl, isopropyl, and butyl, and the halogen atom represented by $Y^2$ includes fluorine, chlorine and bromine.

In the Procedure B, the reaction between (VIII) and (IX) is conducted in an appropriate solvent (e.g. methanol, ethanol, propanol, dioxane, tetrahydrofuran, dimethoxyethane, dimethylsulfoxide, N,N-dimethylformamide), in the presence of a base (e.g. sodium carbonate, potassium carbonate, triethylamine) if necessary, at about 0° -about 100° C. In this reaction a compound (XIII) represented by the formula:

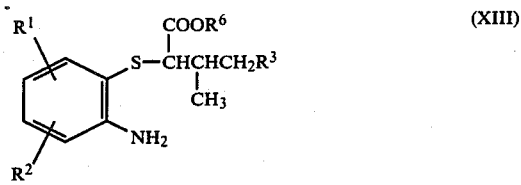

wherein the symbols are the same as described above is first formed as an intermediate, followed by ring closure reaction to give (II-2). Therefore, when this ring closure reaction proceeds only slowly, the ring closure reaction may be accelerated by appropriate heating or by adding an acid (e.g. hydrochloric acid, hydrobromic acid, sulfuric acid, methanesulfonic acid, p-toluenesulfonic acid, acetic acid), either without or after isolation of (XIII).

In Procedure C, (X) and (XI) are allowed to react in the presence of a base to give (XII) which is then reduced to give (II-2). The reaction between (X) and (XI) is conducted in the same solvent as used in Procedure B in the presence of a base (e.g. sodium carbonate, potassium carbonate, sodium hydrogencarbonate, potassium hydrogencarbonate, triethylamine) at about 0°–100° C. The reduction of (XII) is conducted advantageously by using a metal and an acid, such as iron-acetic acid, iron-hydrochloric acid, zinc-acetic acid and tin-hydrochloric acid. Also in this reaction the compound (XIII) is produced as an intermediate, and therefore the ring closure reaction is accelerated by a manner similar to that described in Procedure B.

When optically active starting compounds (VI), (IX) and (XI) are used in the above-mentioned Procedures A-C, optically active products (II) are obtained. Inversion of the absolute configuration occurs in the ring-closure reaction of (VII) to form (II-1) in Procedure A and in the reaction of (VIII) with (IX) to form (II-2) in Procedure B. The absolute configuration of (XI) is retained in Procedure C.

In the following, the results of pharmacological studies to prove the effectiveness of the compounds (I) of this invention in comparison with control compounds are described.

1. Aldose reductase inhibition (in vitro study)

Partially purified aldose reductase from human placenta was used for the test of aldose reductase inhibitory effect according to the method of S. Hayman et al. described in Journal of Biological Chemistry, 240, 877 (1965) or the method of J. H. Kinoshita et al. described in Metabolism, 28, Supplement 1, 462 (1979). The inhibitory activities of each compound at $10^{-6}$ M and at $10^{-7}$ M, expressed in inhibition percentage, are listed in Table 1.

2. Inhibition of sorbitol accumulation in the tissue of experimentally induced diabetic rat Sprague-Dawley rats (male, 5–7-week-old, 5 animals per group) were fasted for 18 hours, and received injection of 70 mg/kg of streptozocin (Cal Biochem Co.) into the caudal vein under anesthesia with ether, so that diabetic rats were obtained. From immediately after the injection of streptozocin these rats were given orally the test compound of 50 mg/kg or 30 mg/kg in the form of 5% gum arabic suspension twice a day (at 10 a.m. and 5 p.m.) for 2 days. During this period the rats were allowed to take CE-2 diet (Clea Japan, Inc.) and water ad libitum. In the morning on the 3rd day (9 a.m.) the rats were killed (decapitation and venesection), and immediately the sciatic nerves were isolated, from which sorbitol was extracted according to the method of M. J. Peterson et al. described in Metabolism, 28, 456 (1979) and the sorbitol level was determined by the enzymatic method of P.S. Clements et al. in Science, 166, 1007 (1969). The results are expressed in percentage (%) taking the value of the untreated control group as 100, and shown in table 1.

TABLE 1

| Compound (Example No.) | in vitro inhibition (%) | | sorbitol accumulation (%) | |
|---|---|---|---|---|
| | $10^{-6}$ M | $10^{-7}$ M | 50 mg/kg | 30 mg/kg |
| 1 | 46.7 | 19.1 | 18**** | 51*** |
| 2 | 43.9 | 8.7 | 12**** | 33**** |
| 3 | 48.9 | 8.9 | 23**** | — |
| 4 | 45.6 | 3.8 | 14**** | 45*** |
| 5 | 48.1 | 17.3 | 11**** | 29**** |
| 6 | 48.2 | 9.4 | 16**** | 33**** |
| 7 | 50.0 | 14.9 | — | 27**** |
| 8 | 50.2 | 9.1 | — | 30**** |
| 9 | 46.4 | 20.0 | 46**** | 60*** |
| 11 | 47.1 | 15.2 | 38**** | 67*** |
| 12 | 43.0 | 19.2 | — | 58** |
| 13 | 46.8 | 14.9 | — | 35*** |
| 17 | 45.7 | 2.6 | — | 62* |
| 19 | 39.3 | 8.0 | — | 15**** |
| 20 | 38.4 | 4.6 | — | 25**** |
| Control[2] | | | | |
| A | 50.8 | 25.0 | 60** | 73 |
| B | 43.1 | 15.7 | 78* | — |
| C | 48.7 | 19.6 | 71* | — |

(Note)
(1) Student's t-test:
*p < 0.05
**p < 0.02
***p < 0.01
****p < 0.001
(2) A: 6-fluoro-3,4-dihydro-3-thioxo-2H—1,4-benzoxazine-4-acetic acid
B: 3,4-dihydro-3-thioxo-2H—1,4-benzothiazine-4-acetic acid
C: 3,4-dihydro-2-methyl-3-thioxo-2H—1,4-benzothiazine-4-acetic acid (Results and Discussion)

As shown in Table 1, although the compounds (I) of this invention were only as effective as or even slightly less effective than the control compounds in inhibition of aldose reductase in vitro, their inhibitory activities of sorbitol accumulation in vivo were superior to those of the control compounds. The difference is particularly evident when the comparison is made between the compound No. 2 with A, and between No. 9 and No. 11 with B and C, which are pairs of compounds having comparable substituents. Treatment of diabetic patients usually requires a long period, and therefore the compounds of this invention which are expected to show excellent effect at a lower dose are very useful as therapeutic agents.

3. Inhibitory action on platelet aggregation

Effect of 3,4-dihydro-2,8-diisopropyl-3-thioxo-2H-1,4-benzoxazine-4-acetic acid on platelet aggregation was examined using washed rat platelets.

(1) Methods

Rat blood was collected into a plastic syringe containing one-tenth volume of 3.8% trisodium citrate from the abdominal aorta of 6-7 weeks old, male Spraque-Dawley rats under ether anesthesia. Platelet rich plasma (PRP) was prepared by centrifuging the blood at 150 xg for 15 min at room temperature. To prepare washed platelets, the PRP was centrifuged at 1500 xg for 10 min and the precipitated platelets were resuspended in Tyrode's solution. The number of platelets used was $7 \times 10^5$ cells/mm$^3$. Platelet aggregation was measured by the turbidmetric method using an aggregometer (Nikko Bioscience, Model PAR-4M, Tokyo). The test compound dissolved in 10 μl of water was added to 250 μl of washed platelet suspension and incubated at 37° C. for 3 min before 10 μl of aggregating agents (5-10 μl/ml of collagen, Nikko Bioscience or 10 μM of ADP, Shigma, St. Louis, Mo., at the final concentration) was added. The percent inhibition of aggregation by the test compound was calculated by dividing the percent aggregation by that observed in the control run, then multiplying by 100.

(2) Results

The test compound inhibited aggregation of washed platelets induced by either collagen or ADP in a dose related manner (Table 2). Its inhibitory action was more potent than that of indomethacin in ADP-induced aggregation.

TABLE 2

| | Test compound (M) | | | | Indomethacin (M) | |
|---|---|---|---|---|---|---|
| Inducer | $3 \times 10^{-5}$ | $6 \times 10^{-5}$ | $10^{-4}$ | $3 \times 10^{-4}$ | $10^{-4}$ | $3 \times 10^{-4}$ |
| Collagen | 74.5 ± 5.5* | 46.5 ± 1.3** | 31.8 ± 0.9** | 24.1 ± 3.4** | 28.5 ± 1.9** | — |
| ADP | — | — | 90.0 ± 6.0 | 42.0 ± 7.1 | 101.5 ± 8.4 | 97.2 ± 6.4 |

Mean ± SD (N = 3).
**p < 0.001 and
*p < 0.01 vs control (water).

4. Acute toxicity

Acute toxicity of 3,4-dihydro-2,8-diisopropyl-3-thioxo-2H-1,4-benzoxazine-4-acetic acid was examined in mice and rats.

(1) Methods

The various doses of the test compound suspended in 5% gum arabic solution were orally administered to male ICR mice (4 weeks old) and male Wistar rats (5 weeks old), and then mortality was observed during 14 days. Each group consisted of 5 animals.

(2) Results

The LD$_{50}$ of the test compound is shown in Table 3.

TABLE 3

| Animal | LD$_{50}$ (mg/kg) |
|---|---|
| Mouse | 1880 |
| Rat | 2830 |

The following Examples and Reference Examples illustrate the present invention more concretely.

EXAMPLE 1

(1) To a solution of 2-isopropyl-2H-1,4-benzoxazin-3(4H)-one (19.1 g) in N,N-dimethylformamide (200 ml), sodium hydride (60% in oil, 4.0 g) was added and stirred at room temperature for 30 minutes, to which a solution of methyl bromoacetate (10 ml) in N,N-dimethylformamide (200 ml) was added dropwise with ice-cooling. After stirring with ice-cooling for 1 hour, the reaction mixture was diluted with water and subjected to extraction with ethyl acetate. The extract was washed with water, dried (MgSO$_4$) and evaporated to dryness, to give methyl 3,4-dihydro-2-isopropyl-3-oxo-2H-1,4-benzoxazine-4-acetate as an oil. Yield was 26.0 g (98.9%).

(2) A mixture of methyl 3,4-dihydro-2-isopropyl-3-oxo-2H-1,4-benzoxazine-4-acetate (26.0 g), phosphorus pentasulfide (44.4 g) and toluene (250 ml) was refluxed for 3 hours with heating. After cooling the insoluble matter was removed by filtration, and the solvent was evaporated off. To the residue, isopropyl ether (200 ml) was added and the insoluble matter was removed by filtration. The solvent was evaporated off, and hexane was added to the residue, to give crystals of methyl 3,4-dihydro-2-isopropyl-3-thioxo-2H-1,4-benzoxazine-4-acetate. Yield was 22.5 g (80.6%). Recrystallization from isopropyl alcohol gave yellow prisms (mp 60°-61° C.).

Elemental analysis for C$_{14}$H$_{17}$NO$_3$S Calc.: C, 60.19; H, 6.13; N, 5.01; Found: C, 59.98; H, 6.18; N, 4.9.

(3) To a solution of methyl 3,4-dihydro-2-isopropyl-3-thioxo-2H-1,4-benzoxazine-4-acetate (16.7 g) in methanol-dioxane (2:3, 150 ml), 2N NaOH (60 ml) was added dropwise in 10 minutes with stirring. After completion of the addition, stirring was continued for further 15 minutes, and the mixture was diluted with water, acidified with 2N HCl, and subjected to extraction with ethyl acetate. The extract was washed with water, and dried (MgSO$_4$), from which the solvent was evaporated off. To the residue, hexane was added, to give crystals of 3,4-dihydro-2-isopropyl-3-thioxo-2H-1,4-benzoxazine-4-acetic acid. Yield was 12.6 g (79.2%). Recrystallization from isopropyl ether-hexane gave yellow prisms (mp 99°-100° C.). Yield was 11.2 g (70.6%).

Elemental analysis for C$_{13}$H$_{15}$NO$_3$S Calc.: C, 58.85; H, 5.70; N, 5.28; Found: C, 58.85; H, 5.69; N, 5.30.

EXAMPLE 2

In the same manner as in Example 1, from the starting substance 6-fluoro-2-isopropyl-2H-1,4-benzoxazin-3(4H)-one, 6-fluoro-3,4-dihydro-2-isopropyl-3-thioxo-2H-1,4-benzoxazine-4-acetic acid was obtained as light yellow prisms (recrystallized from isopropyl ether-hexane). mp 132°-133° C. Overall yield 60.0%.

Elemental analysis for C$_{13}$H$_{14}$FNO$_3$S Calc.: C, 55.11; H, 4.98; N, 4.94; Found: C, 55.13; H, 4.98; N, 4.95.

EXAMPLE 3

In the same manner as in Example 1, from the starting substance 8-chloro-3,4-dihydro-2-isopropyl-2H-1,4-benzoxazine-3(4H)-one, 8-chloro-3,4-dihydro-2-isopropyl-3-thioxo-2H-1,4-benzoxazine-4-acetic acid was obtained as light yellow prisms (recrystallized from isopropyl ether-hexane). mp 144°–145° C. Overall yield 69.5%.

Elemental analysis for $C_{13}H_{14}ClNO_3$ Calc.: C, 52.09; H, 4.71; N, 4.67; Found: C, 52.40; H, 4.76; N, 4.63.

EXAMPLE 4

In the same manner as in Example 1, from the starting substance 8-fluoro-2-isopropyl-2H-1,4-benzoxazin-3(4H)-one, 8-fluoro-3,4-dihydro-2-isopropyl-3-thioxo-2H-1,4-benzoxazine-4-acetic acid was obtained as light yellow prisms (recrystallized from isopropyl ether-hexane). mp 125°–127° C. Overall yield 70.7%.

Elemental analysis for $C_{13}H_{14}FNO_3S$ Calc C, 55.11; H, 4.98; N, 4.94; Found: C, 55.36; H, 5.05; N, 4.96.

EXAMPLE 5

In the same manner as in Example 1, from the starting substance 2-isopropyl-8-methoxy-2H-1,4-benzoxazin-3(4H)-one, 3,4-dihydro-2-isopropyl-8-methoxy-3-thioxo-2H-1,4-benzoxazine-4-acetic acid was obtained as light yellow prisms (recrystallized from isopropyl ether). mp 159°–160° C. Overall yield 69.9%.

Elemental analysis for $C_{14}H_{17}NO_3S$ Calc.: C, 56.93; H, 5.80; N, 4.74; Found: C, 56.99; H, 5.83; N, 4.73.

EXAMPLE 6

In the same manner as in Example 1, from the starting substance 2-isopropyl-8-methyl-2H-1,4-benzoxazin-3(4H)-one, 3,4-dihydro-2-isopropyl-8-methyl-3-thioxo2H-1,4-benzoxazine-4-acetic acid was obtained as yellow needles (recrystallized from isopropyl ether-hexane). mp 148°–149° C. Overall yield 71.7%.

Elemental analysis for $C_{14}H_{17}NO_3S$ Calc.: C, 60.19; H, 6.13; N, 5.01; Found: C, 60.30; H, 6.18; N, 5.01.

EXAMPLE 7

In the same manner as in Example 1, from the starting substance 2-isopropyl-7-methoxy-2H-1,4-benzoxazin-3(4H)-one, 3,4-dihydro-2-isopropyl-7-methoxy-3-thioxo-2H-1,4-benzoxazine-4-acetic acid was obtained as yellow prisms (recrystallized from isopropyl ether-hexane). mp 128°–129° C. Overall yield 68.2%.

Elemental analysis for $C_{14}H_{17}NO_4S$ Calc.: C, 56.93; H, 5.80; N, 4.744; Found: C, 57.11; H, 5.98; N, 4.71.

EXAMPLE 8

In the same manner as in Example 1, from the starting substance 2,8-diisopropyl-2H-1,4-benzoxazin3(4H)-one, 3,4-dihydro-2,8-diisopropyl-3-thioxo-2H-1,4-benzoxazine-4-acetic acid was obtained as yellow prisms (recrystallized from isopropyl ether-hexane). mp 158°–159° C. Overall yield 72.4%.

Elemental analysis Calc.: C, 62.51; 6.98; N, 4.56; Found: C, 62.80; H, 6.90; N, 4.51.

EXAMPLE 9

(1) A solution of 2-isopropyl-2H-1,4-benzoxazin-3(4H)one (62.1 g) in N,N-dimethylformamide (150 ml) was added dropwise to a stirred suspension of sodium hydride (60% in oil, 12.0 g) in N,N-dimethylformamide (180 ml). The mixture was stirred for 30 minutes and a solution of methyl bromoacetate (30 ml) in N,N-dimethylformamide (60 ml) was added dropwise thereto with ice-cooling. The mixture was stirred for further 1 hour with ice-cooling, poured into 1 l of ice water, and subjected to extraction with ethyl acetate. The ethyl acetate layer was washed, dried (MgSO$_4$), and concentrated. The residue was crystallized from hexane to give methyl 3,4-dihydro-2-isopropyl-3-oxo-2H-1,4-benzothiazine-4-acetate as crystals. Yield was 60.3 g (72.0%). Recrystallization from 2-propanol-hexane gave colorless prisms. mp 81°–82° C.

Elemental analysis for $C_{14}H_{17}NO_3S$ Calc.: C, 60.19; H, 6.13; N, 5.01; Found: C, 60.30; H, 6.13; N, 5.04.

(2) A mixture of methyl 3,4-dihydro-2-isopropyl-3-oxo-2H1,4-benzothiazine-4-acetate (50.0 g), phosphorus pentasulfide (79.5 g), and toluene (450 ml) was refluxed for 5.5 hours with stirring. After cooling, the insoluble matter was removed by filtration, and the solvent was evaporated off. To the residue isopropyl ether (300 ml) was added, and the insoluble matter was removed by filtration. The filtrate was concentrated, and the residue was crystallized from 2-propanol, to give methyl 3,4-dihydro-2-isopropyl-3-thioxo-2H-1,4-benzothiazine-4-acetate as crystals. Yield was 27.0 g (51.0%). Recrystallization from 2-propanol gave yellow prisms. mp 99°–100° C.

Elemental analysis for $C_{14}H_{17}NO_2S_2$ Calc.: C, 56.92; H, 5.80; N, 4.74; Found: C, 57.05; H, 5.87; N, 4.73.

(3) Methyl 3,4-dihydro-2-isopropyl-3-thioxo-2H-1,4-benzothiazine-4-acetate (20.65 g) was dissolved in methanol-dioxane (1:2, v/v, 210 ml), to which 2N-NaOH (70 ml) was added dropwise with stirring. The mixture was stirred at room temperature for further 2 hours, diluted with water and acidified with hydrochloric acid. The crystalline precipitate was collected by filtration and recrystallized from 2-propanol-water to give 3,4-dihydro-2-isopropyl-3-thioxo-2H-1,4-benzothiazine-4-acetic acid as yellow prism. Yield was 18.0 g (91.5%). mp 175°–176° C.

Elemental analysis for $C_{13}H_{15}NO_2S_2$ Calc.: C, 55.49; H, 5.37; N, 4.98; Found: C, 55.63; H, 5.43; N, 4.97.

EXAMPLE 10

In the same manner as in Example 9, from the starting substance 8-chloro-2-isopropyl-2H-1,4-benzothiazin-3(4H)-one, 8-chloro-3,4-dihydro-2-isopropyl-3-thioxo-2H-1,4-benzothiazine-4-acetic acid was obtained as yellow prisms (recrystallized from ethanol-water). mp 151°–152° C. Overall yield 63.5%.

Elemental analysis for $C_{13}H_{14}ClNO_2S_2$ Calc.: C, 49.44; H, 4.47; N, 4.43; Found: C, 49.50; H, 4.75; N, 4.42.

EXAMPLE 11

In the same manner as in Example 9, from the starting substance 2-(1-methylpropyl)-2H-1,4-benzothiazin-3(4H)-one (1:1 diastereomer mixture), 3,4-dihydro-2-(1-methylpropyl)-3-thioxo-2H-1,4-benzothiazine-4-acetic acid (1:1 diastereomer mixture) was obtained as yellow prisms (recrystallized from isopropyl ether-hyexane). mp 137°–138° C. Overall yield 43.9%.

Elemental analysis for $C_{14}H_{17}NO_2S_2$ Calc.: C, 56.92; H, 5.80; N, 4.74; Found: C, 57.08; H, 5.99; N, 4.70.

EXAMPLE 12

In the same manner as in Example 1, from the starting substance 8-ethoxy-2-isopropyl-2H-1,4-benzoxazin-3(4H)-one, 8-ethoxy-3,4-dihydro-2isopropyl3-thioxo-2H-1,4-benzoxazine-4-acetic acid was obtained as yellow prisms (recrystallized from isopropyl etherhexane). mp 138°–139° C. Overall yield 72.4%.

Elemental analysis for $C_{15}H_{19}NO_4S$ Calc.: C, 58.23; H, 6.19; N, 4.53; Found: C, 58.45; H, 6.23; N, 4.59.

EXAMPLE 13

In the same manner as in Example 1, from the starting substance 8-ethyl-2-isopropyl-2H-1,4-benzoxazin3(4H)-one, 8-ethyl-3,4-dihydro-2-isopropyl-3-thioxo-2H-1,4-benzoxazine-4-acetic acid was obtained as yellow prisms (recrystallized from isopropyl ether-hexane). mp 117°–118° C. Overall yield 73.1%.

Elemental analysis for $C_{15}H_{19}NO_3S$ Calc.: C, 61.41; H, 6.53; N, 4.77; Found: C, 61.55; H, 6.55; N, 4.81.

EXAMPLE 14

In the same manner as in Example 1, from the starting substance 2-(1-methylpropyl)-2H-1,4-benzoxazin3(4H)-one (1:1 diastereomer mixture), 3,4-dihydro-2-(1-methylpropyl)-3-thioxo-2H-1,4-benzoxazine-4-acetic acid (1:1 diastereomer mixture) was obtained as yellow prisms (recrystallized from isopropyl ether-hexane). mp 70°–72° C. Yield 44.8%.

EXAMPLE 15

In the same manner as in Example 1, from the starting substance 2-isopropyl-6-methyl-2H-1,4-benzoxazin-3(4H)-one, 3,4-dihydro-2-isopropyl-6-methyl-3-thioxo-2H-1,4-benzoxazine-4-acetic acid was obtained as yellow prisms (recrystallized from isopropyl ether-hexane). mp 144°–145° C. Overall yield 76.7%.

EXAMPLE 16

In the same manner as in Example 1, from the starting substance 2-isopropyl-7-methyl-2H-1,4-benzoxazin-3(4H)one, 3,4-dihydro-2-isopropyl-7-methyl-3-thioxo-2H-1,4-benzoxazine-4-acetic acid was obtained as yellow prisms (recrystallized from isopropyl ether-hexane). mp 146°–147° C. Yield 72.2%.

EXAMPLE 17

In the same manner as in Example 1, from the starting substance 7-fluoro-2-isopropyl-2H-1,4-benzoxazin-3(4H)-one, 7-fluoro-3,4-dihydro-2isopropyl3-thioxo-2H-1,4-benzoxazine-4-acetic acid was obtained as yellow prisms (recrystallized from isopropyl etherhexane). mp 113°–114° C. Overall yield 62.4%.

EXAMPLE 18

In the same manner as in Example 1, from tne starting substance 2-isopropyl-6-methoxy-2H-1,4-benzoxazin-3(4H)-one, 3,4-dihydro-2-isopropyl-6-methoxy-3-thioxo-2H-1,4-benzoxazine-4-acetic acid was obtained as yellow plates (recrystallized from isopropyl etherhexane). mp 140°–141° C. Overall yield 77.8%.

EXAMPLE 19

In the same manner as in Example 1, from the starting substance 8-t-butyl-2-isopropyl-2H-1,4-benzoxazin-3(4H)-one, 8-t-butyl-3,4-dihydro-2-isopropyl-3-thioxo-2H-1,4-benzoxazine-4-acetic acid was obtained as light yellow prisms (recrystallized from isopropyl ether) mp 188°–189° C. Yield 68.9%.

EXAMPLE 20

In the same manner as in Example 1, from the starting substance 8-cyclohexyl-3,4-dihydro-2-isopropyl-2H-1,4-benzoxazin3(4H)-one, 8-cyclohexyl-3,4-dihydro-2-isopropyl-3-thioxo2H-1,4-benzoxazine-4-acetic acid was obtained as light yellow prisms (recrystallized from ethanol). mp 164°–165° C. Overall yield 81.7%.

EXAMPLE 21

A mixture of 3,4-dihydro-2,8-diisopropyl-3-thioxo-2H-1,4-benzoxazine-4-acetic acid (6.14 g), (S)-methyl lactate (8.32 g), 4-dimethylaminopyridine (1.22 g), dicyclohexylcarbodiimide (4.94 g) and dichloromethane (80 ml) was stirred at room temperature for 18 hours. The precipitate was filtered off and the filtrate was concentrated. The residue was chromatographed on silica gel (400 g) using hexane-ethyl ether (95:5, v/v) as the eluent to give the following two compounds. (S)-Methyl 2-[(R)-3,4-dihydro-2,8-diisopropyl-3-thioxo-2H-1,4-benzoxazin-4-yl]acetoxypropionate: oil. Yield 1.55 g. $[\alpha]_D^{22.5}+61.2°$ (c=0.35, MeOH).

NMR (CDCl$_3$) δ: 0.97 (3H, d, J=7.5 Hz), 1.07 (3H, d, J=7.5 Hz), 1.20 (3H, d, J=7.5 Hz), 1.27 (3H, d, J=7.5 Hz), 1.55 (3H, d, J=7.5 Hz), 2.35 (1H, sext., J=7.5 Hz), 3.43 (1H, quin., J=7.5 Hz), 3.77 (3H, s), 4.73 (1H, d, J=18 Hz), 4.87 (1H, d, 7.5 Hz), 5.23 (1H, q, J=7.5 Hz), 5.93 (1H, d, J=18 Hz), 6.71–7.08 (3H, m)

(S)-Methyl 2-[(S)-3,4-dihydro-2,8-diisopropyl-3-thioxo2H-1,4-benzoxazin-4-yl]acetoxypropionate: oil. Yield 1.2 g. $[\alpha]_D^{22.5}-78°$ (c=0.4, MeOH).

NMR (CDCl$_3$) δ: 0.98 (3H, d, J=7.5 Hz), 1.05 (3H, d, J=7.5 Hz), 1.18 (3H, d, J=7.5 Hz), 1.30 (3H, d, J=7.5 Hz), 1.48 (3H, d, J=7.5 Hz), 2.45 (1H, sext., J=7.5 Hz), 3.25-3.58 (1H, m), 3.73 (3H, s), 4.7 g (1H, d, J=7.5 Hz), 5.00 (1H, d, J=18 Hz), 5.18 (1H, q, J=7.5 Hz), 5.60 (1H, d, J=18 Hz), 6.73–7.05 (3H, m)

EXAMPLE 22

A stirred solution of (S)-Methyl 2-[(R)-3,4-dihydro-2,8-diisopropyl-3-thioxo-2H-1,4-benzoxazin-4-yl]acetoxypropionate (1.55 g) in a mixture of dioxane (10 ml) and MeOH (10 ml) was treated with 2N-NaOH (10 ml) at room temperature for 30 minutes. The mixture was acidified with HCl, diluted with water and extracted with ethyl acetate. The ethyl acetate layer was washed with water, dried over MgSO$_4$, and concentrated. The residue was treated with hexane to yield 0.12 g of crystals of (±)-3,4-dihydro-2,8-diisopropyl-3-thioxo- 2H-1,4-benzoxazine-4-acetic acid which formed as a result of slight racemization of the product. The mother liquor was concentrated and the residue was dissolved in hexane. When the solution was allowed to stand, (R)-(+)-3,4-dihydro-2,8-diisopropyl-3-thioxo-2H-1,4-benzoxazine-4-acetic acid was obtained as crystals (0.55 g), mp 110°–111° C. $[\alpha]_D^{24}+107.2°$ (c=0.45, MeOH).

Elemental analysis for $C_{16}H_{21}NO_3S$
Calc. C, 62.51; H, 6.89; N, 4.56
Found: C, 62.79; H, 6.99; N, 4.52

EXAMPLE 23

(S)-Methyl 2-[(S)-3,4-dihydro-2,8-diisopropyl-3-thioxo-2H-1,4-benzoxazin-4-yl]acetoxypropionate (1.1 g) was hydrolyzed and worked up in the manner same as that used in Example 22 to yield (S)-(-)-3,4-dihydro-2,8-diisopropyl-3-thioxo-2H-1,4-benzoxazine-4-acetic acid (0.53 g), mp 109°–110° C. $[\alpha]_D^{23}-105°$ MeOH).

Elemental analysis for $C_{16}H_{21}NO_3S$
Calc.: C, 62.51; H, 6.89; N, 4.56.
Found C, 62.86; H, 6.93; N, 4.55.

EXAMPLE 24

(1) To a solution of (S)-2,8-diisopropyl-2H-1,4-benzoxazin-3(4H)-one (4.66 g) in dimethylformamide (60 ml), was added portionwise 60% sodium hydride in oil (0.84 g). The mixture was stirred at room temperature for 10 minutes, and a solution of methyl bromoacetate (2.0 ml) in dimethylformamide (6.0 ml) was added thereto. The whole was stirred at room temperature for 30 minutes, diluted with water, and extracted with ethyl acetate. The ethyl acetate layer was washed with water, dried (MgSO$_4$) and concentrated. The residue was crystallized from hexane to yield (S)-methyl 3,4-dihydro-2,8-diisopropyl-3-oxo-2H-1,4-benzoxazine-4-acetate as crystals (4.95 g, 81.1%). Recrystallization from hexane gave colorless needles, mp 67°–68° C. $[\alpha]_D^{23}$+3.7° (c=0.95, MeOH).

Elemental analysis for C$_{17}$H$_{23}$NO$_4$
Calc.: C, 66.86; H, 7.59; N, 4.59
Found: C, 66.90; H, 7.69; N, 4.56

(2) A mixture of (S)-methyl 3,4-dihydro-2,8-diisopropyl-3-oxo-2H-1,4-benzoxazine-4-acetate (3.05 g), 2,4-bis(methylthio)-1,3,2,4-dithiadiphosphetan-2,4-disulfide (Davy reagent methyl)(2.84 g) and toluene (60 ml) was stirred at 50° C. for 64 hours. The insoluble material was filtered off and the filtrate was concentrated. The residue was purified by column chromatography on silica gel (100 g) using hexane-ethyl ether (85:15, v/v) as the eluent to yield (S)-methyl 3,4-dihydro-2,8-diisopropyl-3-thioxo-2H-1,4-benzoxazine-4-acetate as an oil (3.00 g).

(3) The oil obtained in (2) was dissolved in a mixture of dioxane (9 ml) and MeOH (9 ml), and 2N-NaOH (9.3 ml) was added thereto. The whole was stirred at room temperature for 45 minutes, diluted with water, acidified with hydrochloric acid, and extracted with ethyl acetate. The ethyl acetate layer was washed with water, dried (MgSO$_4$) and concentrated. The residue was treated with hexane to yield the racemized compound, (±)-3,4-dihydro-2,8-diisopropyl-3-thioxo-2H-1,4-benzoxazine4-acetic acid (0.8 g). The mother liquor was concentrated and the residue was crystallized from hexane to yield (S)-(−)-3,4-dihydro-2,8-diisopropyl-3-thioxo-2H1,4-benzoxazine-4-acetic acid (1.28 g, 41.7%), mp 109°–110° C. $[\alpha]_D^{22}$−101.1° (c=0.71, MeOH)

Preparation Examples (Tablets)

The compounds (I) of this invention can be used as therapeutic agents for diabetic complications, for example, according to the following prescription.

| | | |
|---|---|---|
| (1) 3,4-dihydro-2-isopropyl-8-methyl-3-thioxo-2H—1,4-benzoxazine-4-acetic acid | | 100 g |
| (2) lactose | | 50 g |
| (3) corn starch | | 15 g |
| (4) calcium carboxymethylcellulose | | 44 g |
| (5) magnesium stearate | | 1 g |
| | 1000 tablets | 210 g |

The entire amounts of (1), (2), and (3) and 30 g of (4) were kneaded with water, dried under reduced pressure, and granulated. To the granules 14 g of (4) and 1 g of (5) were added, mixed, and compressed by compressor to produce 1000 tablets containing 100 mg of (1) per tablet.

(Eye Drops)

By routine method, an eye drop composition was prepared according to the following formula.

| | |
|---|---|
| 3,4-dihydro-2-isopropyl-8-methoxy-3-thioxo-2H—1,4-benzoxazine-4-acetic acid | 0.05 g |
| polysorbate 80 | 0.2 g |
| monobasic sodium phosphate dihydrate | 0.2 g |
| dibasic sodium phosphate dodecahydrate | 0.5 g |
| sodium chloride | 0.75 g |
| methyl p-hydroxybenzoate | 0.026 g |
| propyl p-hydroxybenzoate | 0.014 g |
| sterile purified water | sufficient quantity |
| total | 100 ml |

(Eye Ointment)

By a routine method, eye ointment was prepared according to the following formula.

| | |
|---|---|
| 3,4-dihydro-2-isopropyl-3-thioxo-2H—1,4-benzoxazine-4-acetic acid | 0.1 g |
| liquid paraffin | 1 g |
| white petrolatum | sufficient quantity |
| total | 100 g |

REFERENCE EXAMPLE 1

(1) To a mixture of 2-aminophenol (27 25 g), sodium hydrogencarbonate (31.5 g), ethyl acetate (250 ml), and water (200 ml), a solution of 2-bromo-3-methylbutyryl chloride (49.8 g) in ethyl acetate (100 ml) was added dropwise with ice-cooling and with stirring. After stirring with ice-cooling for further 1 hour, the ethyl acetate layer was separated, washed with water, and dried (MgSO$_4$), and the solvent was evaporated off. The residue was crystallized from hexane, to give 2-(2-bromo-3-methylbutyryl)aminophenol. Yield was 59.7 g (87.9%). Recrystallization from isopropyl ether gave colorless prisms, mp 110°–111° C.

(2) A mixture of 2-(2-bromo-3-methylbutyryl)aminophenol (58.0 g), powdered potassium carbonate (38.3 g) and N,N-dimethylformamide (200 ml) was stirred at room temperature for 2 hours. The mixture was diluted with water and the precipitate was collected to yield 2-isopropyl-2H-1,4-benzoxazin-3(4H)-one as crystals. Yield was 38.1 g (93.4%). Recrystallization from ethanol gave colorless plates, mp 118°–119° C. In the same manner as in Reference Example 1, the following compounds were obtained.

REFERENCE EXAMPLE 2

(1) 2-(2-bromo-3-methylbutyryl)amino-4-fluorophenol: mp 93°–94° C. (recrystallized from isopropyl ether-hexane). Yield 81.9%.

(2) 6-fluoro-2-isopropyl-2H-1,4-benzoxazin-3(4H)-one: mp 138°–139° C. (recrystallized from ethanol). Yield 94.0%.

REFERENCE EXAMPLE 3

(1) 2-(2-bromo-3-methylbutyryl)amino-6-chlorophenol: mp 98°–99° C. (recrystallized from isopropyl ether-hexane). Yield 52.3%.

(2) 8-chloro-2-isopropyl-2H-1,4-benzoxazin-3(4H)-one: mp 132°–133° C. (recrystallized from ethanol). Yield 84.6%.

REFERENCE EXAMPLE 4

(1) 2-(2-bromo-3-methylbutyryl)amino-6-fluorophenol: mp 123°–124° C. (recrystallized from isopropyl ether). Yield 88.5%.

(2) 8-fluoro-2-isopropyl-2H-1,4-benzoxazin-3(4H)-one: mp 146°–147° C. (recrystallized from ethanol-water). Yield 91.0%.

REFERENCE EXAMPLE 5

(1) 2-(2-bromo-3-methylbutyryl)amino-6-methoxyphenol: oil.

(2) 2-isopropyl-8-methoxy-2H-1,4-benzoxazin-3(4H)-one: mp 149°–150° C. (recrystallized from ethanol-water). Overall yield 56.2%.

REFERENCE EXAMPLE 6

(1) 2-(2-bromo-3-methylbutyryl)amino-6-methylphenol: mp 109°–110° C. (recrystallized from isopropyl ether). Yield 87.4%.

(2) 2-isopropyl-8-methyl-2H-1,4-benzoxazin-3(4H)-one: mp 109°–110° C. (recrystallized from ethanol-water). Yield 91.9%.

REFERENCE EXAMPLE 7

(1) 2-(2-bromo-3-methylbutyryl)amino-5-methoxyphenol: mp 143°–144° C. (recrystallized from ethyl acetate). Yield 87.5%.

(2) 2-isopropyl-7-methoxy-2H-1,4-benzoxazin-3(4H)-one: mp 126°–127° C. (recrystallized from ethanol). Yield 86.9%.

REFERENCE EXAMPLE 8

(1) 2-(2-bromo-3-methylbutyryl)amino-6-isopropylphenol: mp 90°–91° C. (recrystallized from isopropyl ether-hexane). Yield 71.6%.

(2) 2,8-diisopropyl-2H-1,4-benzoxazin-3(4H)-one: mp 129°–130° C. (recrystallized from ethanol). Yield 95.2%.

REFERENCE EXAMPLE 9

To a mixture of methyl 2-bromo-3-methylacetate (78.0 g), powdered potassium carbonate (55.2 g), and N,N-dimethylformamide (400 ml), 2-aminothiophenol (50.0 g) was added dropwise with stirring. After stirring at room temperature for further 1 hour, concentrated hydrochloric acid (60 ml) was added dropwise. The mixture was heated at 80° C. for 30 minutes, and diluted with water. The resulting precipitate of 2-isopropyl-2H-1,4-benzothiazin-3(4H)-one (76.0 g, 91.8%) was collected by filtration. Recrystallization from ethanol gave colorless needles, mp 152°–153° C.

Elemental analysis for $C_{11}H_{13}NOS$
Calc.: C, 63.74; H, 6.32; N, 6.76.
Found: C, 63.84; H, 6.23; N, 6.761.

REFERENCE EXAMPLE 10

(1) A mixture of 2,3-dichloronitrobenzene (3.84 g), methyl 2-mercapto-3-methylbutyrate (2.96 g), potassium carbonate (2.37 g), and N,N-dimethylformamide (40 ml) was stirred at room temperature for 5 hours, diluted with water and extracted with ethyl acetate. The ethyl acetate layer was washed with water and dried (MgSO$_4$), from which the solvent was evaporated off, to give quantitatively methyl 2-(2-chloro-6-nitrophenylthio)-3-methylbutyrate as an oil.

(2) The oil described above was dissolved in acetic acid-water (3:1, 40 ml), to which iron powder (6.72 g) was added portionwise with stirring. After stirring at room temperature for 40 minutes, the precipitate was removed by filtration and washed with hot N,N-dimethylformamide. The filtrate and the washings were combined and diluted with water, to give crystals of 8-chloro-2-isopropyl-2H-1,4-benzothiazin-3(4H)-one. Yield was 3.46 g (83.0%). Recrystallization from methanol gave colorless plates, mp 158°–159° C. Yield was 3.46 g (71.8%). Elemental analysis
Calc.: C, 54.65; H, 5.00; N, 5.79
Found C, 54.63; H, 5.04; N, 5.69

REFERENCE EXAMPLE 11

In the same manner as in Reference Example 9, methyl 2-bromo-3-methylvalerate (1:1 diastereomer mixture) and 2-aminothiophenol were allowed to react followed by ring closure reaction, to give 2-(1-methylpropyl)-2H-1,4-benzothiazin-3(4H)-one (1:1 diastereomer mixture) as colorless prisms. mp 99°–100° C. (recrystallized from ethanol). Yield 72.6%.

In the same manner as in Reference Example 1, the following compounds were obtained.

REFERENCE EXAMPLE 12

(1) 2-(2-bromo-3-methylbutyryl)amino-6-ethoxyphenol: oil (2) 8-ethoxy-2-isopropyl-2H-1,4-benzoxazin-3(4H)-one: mp 129°–130° C. (recrystallized from etnanol-water). Overall yield 87.2%.

REFERENCE EXAMPLE 13

(1) 2-(2-bromo-3-methylbutyryl)amino-6-ethylphenol: mp 106°–107° C. (recrystallized from isopropyl ether). Yield 83.3%.

(2) 8-ethyl-2-isopropyl-2H-1,4-benzoxazin-3(4H)-one: mp 93°–94° C. (recrystallized from isopropyl ether). Yield 93.9%.

REFERENCE EXAMPLE 14

(1) 2-(2-bromo-3-methylvaleryl)aminophenol (1:1 diastereomer mixture): mp 108°–109° C. (recrystallized from isopropyl ether-hexane). Yield 81.6%.

(2) 2-(1-methylpropyl)-2H-1,4-benzoxazin-3(4H)-one (1:1 diastereomer mixture): mp 94°–95° C. (recrystallized from ethanol-water). Yield 90.1%.

REFERENCE EXAMPLE 15

(1) 2-(2-brcmo-3-methylbutyryl)amino-4-methylphenol: mp 119°–120° C. (recrystallized from isopropyl ether). Yield 89.7%.

(2) 2-isopropyl-6-methyl-2H-1,4-benzoxazin-3(4H)-one: mp 131°–132° C. (recrystallized from ethanol). Yield 91.8%.

REFERENCE EXAMPLE 16

(1) 2-(2-bromo-3-methylbutyryl)amino-5-methylphenol: mp 109°–110° C. (recrystallized from isopropyl ether). Yield 85.1%.

(2) 2-isopropyl-7-metnyl-2H-1,4-benzoxazin-3(4H)-one: mp 129°–130° C. (recrystallized from ethanol-water). Yield 95.2%.

REFERENCE EXAMPLE 17

(1) 2-(2-bromo-3-methylbutyryl)amino-5-fluorophenol: mp 105°–106° C. (recrystallized from isopropyl ether-hexane). Yield 85.1%.

(2) 7-fluoro-2-isopropyl-2H-1,4-benzoxazin-3(4H)-one: mp 178°–179° C. (recrystallized from ethanol). Yield 96.0%.

REFERENCE EXAMPLE 18

(1) 2-(2-bromo-3-methylbutyryl)amino-4-methoxyphenol: mp 130°–131° C. (recrystallized from isopropyl ether). Yield 88.4%.

(2) 2-isopropyl-6-methoxy-2H-1,4-benzoxazin-3(4H)-one: mp 129°–130° C. (recrystallized from ethanol-water). Yield 91.0%.

REFERENCE EXAMPLE 19

(1) 2-(2-bromo-3-methylbutyryl)amino-6-t-butylphenol: mp 103°–104° C. (recrystallized from isopropyl ether). Yield 77.2%.

(2) 8-t-butyl-2-isopropyl-2H-1,4-benzoxazin-3(4H)-one: mp 170°–171° C. (recrystallized from ethanol). Yield 75.7%.

REFERENCE EXAMPLE 20

(1) 2-(2-bromo-3-methylbutyryl)amino-6-cyclohexylphenol: oil. Yield 95.0%

(2) 8-cyclohexyl-2-isopropyl-2H-1,4-benzoxazin-3(4H)-one: mp 164°–165° C. (recrystallized from ethanol). Yield 81.7%.

REFERENCE EXAMPLE 21

(1) To a stirred, ice-cooled mixture of 2-amino-6-isopropylphenol hydrochloride (15.0 g), ethyl acetate (200 ml), water (100 ml), and sodium bicarbonate (20.0 g), was added dropwise a solution of (R)-2-bromo-3-methylbutyryl chloride (16.0 g) in ethyl acetate (30 ml). The whole was stirred for 30 minutes, and the ethyl acetate layer was separated, washed with water and dried over MgSO4. Removal of the solvent gave (R)-2-(2-bromo-3-methylbutyryl)amino-6-isopropylphenol as crystals (19.1 g, 76.1%). Recrystallization from isopropyl ether afforded colorless needles, mp 108°–109° C. $[\alpha]_D^{23} + 44.8°$ (c=0.82, MeOH).

Elemental analysis for $C_{14}H_{20}BrNO_2$
Calc.: C, 53.51; H, 6.42; N, 4.46.
Found: C, 53.48; H, 6.45; N, 4.42.

(2) A solution of (R)-2-(2-bromo-3-methylbutyryl)amino-6-isopropylphenol (18.5 g) in dimethylformamide (120 ml) was treated with powdered potassium carbonate (9.75 g) at room temperature for 3 hours. Dilution with water gave crystals, which were recrystallized from 2-propanol to yield (S)-2,8-diisopropyl-2H-1,4-benzoxazin-3(4H)-one as colorless prisms (11.0 g, 80.3%), mp 151°–152° C., $[\alpha]_D^{23} - 5.6°$ (c=1.0, MeOH).

Elemental analysis for $C_{14}H_{19}NO_2$
Calc.: C, 72.07; H, 8.21; N, 6.00.
Found: C, 72.06; H, 8.28; N, 5.97.

We claim:

1. A compound of the formula:

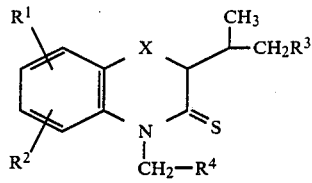

wherein, $R^1$ and $R^2$ are, the same or different, hydrogen, a halogen, a lower alkyl, a cycloalkyl having 3°–7 carbon atoms, a lower alkoxy, trifluoromethyl or a phenylalkoxy having 7–9 carbon atoms whose phenyl ring may be substituted by one or three substituents selected from the group consisting of a halogen, a lower alkyl, a lower alkoxy, methylenedioxy and trifluoromethyl;

$R^3$ is hydrogen or methyl;
$R^4$ is carboxyl or an esterified carboxyl; and
X is oxygen or sulfur,
or a pharmaceutically acceptable salt thereof.

2. A compound as claimed in claim 1, wherein X is oxygen.

3. A compound as claimed in claim 1, wherein one of $R^1$ and $R^2$ is hydrogen and the other is a lower alkyl.

4. A compound as claimed in claim 1, wherein the compound is 8-ethyl-3,4-dihydro-2-isopropyl-3-thioxo-2H-1,4-benzoxazine-4-acetic acid.

5. A compound as claimed in claim 1, wherein the compound is 3,4-dihydro-2,8-diisopropyl-3-thioxo-2H-1,4-benzoxazine-4-acetic acid.

6. A compound as claimed in claim 1, wherein the compound is 8-t-butyl-3,4-dihydro-2-isopropyl-3-thioxo-2H-1,4-benzoxazine-4-acetic acid.

7. A compound as claimed in claim 1, wherein the compound is 8-cyclohexyl-3,4-dihydro-2-isopropyl-3-thioxo-2H-1,4-benzoxazine-4-acetic acid.

8. A therapeutic agent for prevention and treatment of diabetic complication, which comprises, as an active ingredient, an effective amount of a compound of the formula:

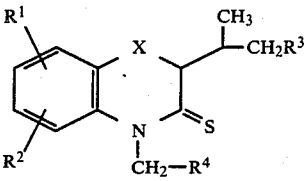

wherein
$R^1$ and $R^2$ are, the same or different, hydrogen, a halogen, a lower alkyl, a cycloalkyl having 3–7 carbon atoms, a lower alkoxy, trifluormethyl or a phenylalkoxy having 7–9 carbon atoms whose phenyl ring may be substituted by one to three substituents selected from the group consisting of a halogen, a lower alkyl, a lower alkoxy, methylenedioxy and trifluoromethyl;
$R^3$ is hydrogen or methyl;
$R^4$ is carboxyl or an esterified carboxyl; and
X is oxygen or sulfur,
or a pharmaceutically acceptable salt thereof, and a pharmaceutically acceptable carrier or excipient therefor.

* * * * *